US006790231B2

United States Patent
Liddicoat et al.

(10) Patent No.: US 6,790,231 B2
(45) Date of Patent: Sep. 14, 2004

(54) APPARATUS AND METHOD FOR REDUCING MITRAL REGURGITATION

(75) Inventors: John R. Liddicoat, Sewickley, PA (US); Steven B. Woolfson, Boston, MA (US); Richard B. Streeter, Winchester, MA (US); William E. Cohn, Chestnut Hill, MA (US)

(73) Assignee: Viacor, Inc., Wilmington, MA (US)

( * ) Notice: Subject to any disclaimer, the term of this patent is extended or adjusted under 35 U.S.C. 154(b) by 0 days.

(21) Appl. No.: 10/068,700

(22) Filed: Feb. 5, 2002

(65) Prior Publication Data

US 2002/0183836 A1 Dec. 5, 2002

Related U.S. Application Data

(60) Provisional application No. 60/266,766, filed on Feb. 5, 2001.

(51) Int. Cl.[7] .................................................... A61F 2/06
(52) U.S. Cl. ...................................... 623/2.37; 623/2.36
(58) Field of Search ................................. 623/1, 2, 900, 623/904; 600/37; 606/108, 191–198, 139; 128/898

(56) References Cited

U.S. PATENT DOCUMENTS

| | | |
|---|---|---|
| 4,669,473 A | 6/1987 | Richards et al. |
| 4,917,698 A | 4/1990 | Carpentier et al. |
| 5,061,277 A | 10/1991 | Carpentier et al. |
| 5,092,889 A | 3/1992 | Campbell, Jr. |
| 5,269,809 A | 12/1993 | Hayhurst et al. |
| 5,332,402 A | 7/1994 | Teitelbaum |
| 5,389,091 A | 2/1995 | Moorehead |
| 5,443,481 A | 8/1995 | Lee |
| 5,545,209 A | 8/1996 | Roberts et al. |
| 5,720,726 A | 2/1998 | Marcadis et al. |
| 5,755,781 A | 5/1998 | Jayaraman |
| 5,800,495 A | 9/1998 | Machek et al. |
| 5,800,526 A | 9/1998 | Anderson et al. |

(List continued on next page.)

FOREIGN PATENT DOCUMENTS

| | | |
|---|---|---|
| JP | 409322936 A | 12/1997 |
| WO | WO 01/00111 A1 | 1/2001 |
| WO | WO 01/54618 A1 | 8/2001 |
| WO | WO 02/053206 A2 | 7/2002 |
| WO | WO 02/060352 A1 | 8/2002 |
| WO | WO 02/062270 A1 | 8/2002 |
| WO | WO 02/091908 A1 | 11/2002 |
| WO | WO 02/100240 A2 | 12/2002 |
| WO | WO 03/037171 A2 | 5/2003 |

OTHER PUBLICATIONS

Alferness et al., U.S. patent application Publication No. US 2002/0087173 A1, published Jul. 4, 2002.

(List continued on next page.)

*Primary Examiner*—David J. Isabella
*Assistant Examiner*—Urmi Chattopadhyay
(74) *Attorney, Agent, or Firm*—Pandiscio & Pandiscio

(57) ABSTRACT

Apparatus for reducing mitral regurgitation, including a bendable elongated body adapted to be inserted into the coronary sinus of a patient in the vicinity of the posterior leaflet of the mitral valve, the elongated body being adjustable between a first configuration adapted to be delivered into the coronary sinus and a second configuration adapted to exert a force onto the posterior annulus. The body includes a flexible spine having a proximal end and a distal end, and a flexible wire mounted on the spine and having a distal end fixed to the spine proximate to the distal end of the spine, and having a proximal portion extending from the proximal end of the spine. Axial movement of the wire causes a change in the spine from the first configuration to the second configuration to exert the force on the posterior annulus and thereby reduce mitral regurgitation.

13 Claims, 7 Drawing Sheets

U.S. PATENT DOCUMENTS

| | | | |
|---|---|---|---|
| 5,855,565 | A | 1/1999 | Bar-Cohen et al. |
| 5,957,949 | A | 9/1999 | Leonhardt et al. |
| 5,980,570 | A | 11/1999 | Simpson |
| 5,984,917 | A | 11/1999 | Fleischman et al. |
| 6,033,436 | A | 3/2000 | Steinke et al. |
| 6,051,020 | A | 4/2000 | Goicoechea et al. |
| 6,071,263 | A | 6/2000 | Kirkman |
| 6,086,599 | A | 7/2000 | Lee et al. |
| 6,090,136 | A | 7/2000 | McDonald et al. |
| 6,162,245 | A | 12/2000 | Jayaraman |
| 6,165,194 | A | 12/2000 | Denardo |
| 6,187,040 | B1 | 2/2001 | Wright |
| 6,210,432 | B1 | 4/2001 | Solem et al. |
| 6,241,746 | B1 | 6/2001 | Bosma et al. |
| 6,258,117 | B1 | 7/2001 | Camrud et al. |
| 6,277,107 | B1 * | 8/2001 | Lurie et al. .................. 604/528 |
| 6,328,765 | B1 | 12/2001 | Hardwick et al. |
| 6,332,896 | B1 | 12/2001 | Hubbard et al. |
| 6,402,781 | B1 | 6/2002 | Langberg et al. |
| 6,419,696 | B1 | 7/2002 | Ortiz et al. |
| 6,537,314 | B2 | 3/2003 | Langberg et al. |
| 6,569,198 | B1 | 5/2003 | Wilson et al. |
| 6,602,288 | B1 * | 8/2003 | Cosgrove et al. .......... 623/2.36 |
| 6,656,221 | B2 | 12/2003 | Taylor et al. |
| 2001/0052345 | A1 * | 12/2001 | Niazi ......................... 128/898 |
| 2003/0093148 | A1 | 5/2003 | Bolling et al. |

OTHER PUBLICATIONS

Langberg et al., U.S. patent application Publication No. US 2002/0103532 A1, published Aug. 1, 2002.

Langberg et al., U.S. patent application Publication No. US 2002/0103533 A1, published Aug. 1, 2002.

Lashinshi et al., U.S. patent application Publication No. US 2002/0151961 A1, published Oct. 17, 2002.

Mathis, U.S. patent application Publication No. US 2002/0169502 A1, published Nov. 14, 2002.

Alfreness et al., U.S. patent application Publication No. US 2002/0169504 A1, published Nov. 14, 2002.

Solem et al., U.S. patent application Publication No. US 2003/0069636 A1, published Apr. 10, 2003.

Adams et al., U.S. patent application Publication No. US 2003/0083538 A1, published May 1, 2003.

Alfreness et al., U.S. patent application Publication No. US 2003/0105520 A1, published Jun. 5, 2003.

Langberg et al., U.S. patent application Publication No. US 2001/0044568 A1, published Nov. 22, 2001.

Langberg et al., U.S. patent application Publication No. US 2002/0016628 A1, published Feb. 7, 2002.

Solem et al., U.S. patent application Publication No. US 2001/0018611 A1, published Aug. 30, 2001.

Buchanan, James W., Circumferential Suture of the Mitral Annulus for Correction of Mitral Regurgitation in Dogs, Veterinary Surgery, 1998, pp. 182–193.

Kerstetter, Kyle K. et al., Short–Term Hemodynamic Evaluation of Circumferential Mitral Annuloplasty for Correction of Mitral Valve Regurgitation in Dogs, Veterinary Surgery, 1998, pp. 216–223.

Beardow, Andrew W. et al., Chronic Mitral Valve Disease in Cavalier King Charles Spaniels: 95 Cases (1987–1991), JAVMA, vol. 203, No. 7, Oct. 1, 1993, pp. 1023–1029.

Davila, Julio C. et al., Circumferential Suture of The Mitral Ring, 18 pages.

Glover, Robert P. et al., The Treatment of Mitral Valve Insufficiency By The Purse–String Technique, The Journal of Thoracic Surgery, Jan. 1957, 14 pages.

Davila, Julio C. et al., Circumferential Suture of The Mitral Valve for the Correction of Regurgitation, The American Journal of Cardiology, Inc., Sep. 1958, 6 pages.

Buchanan, James W., Causes and Prevalence of Cardiovascular Disease, Current Veterinary Therapy XI, WB Saunders Co., 1992, 2 pages.

* cited by examiner

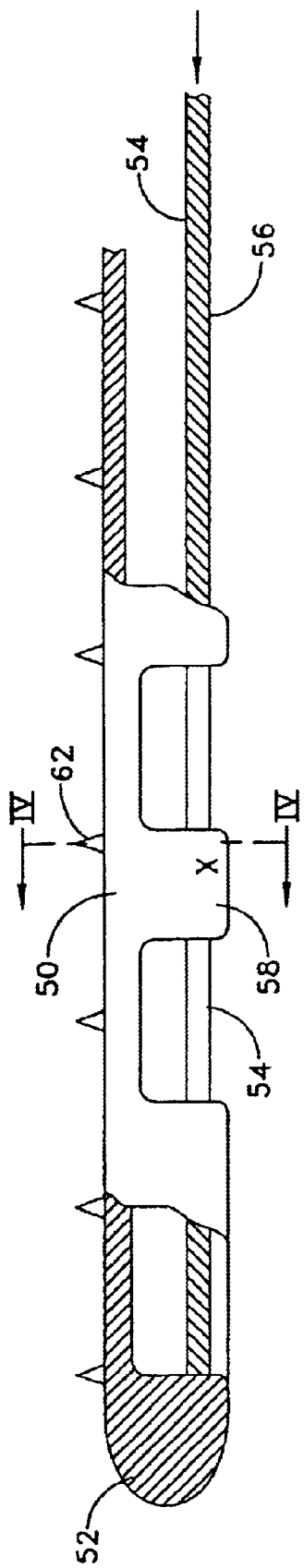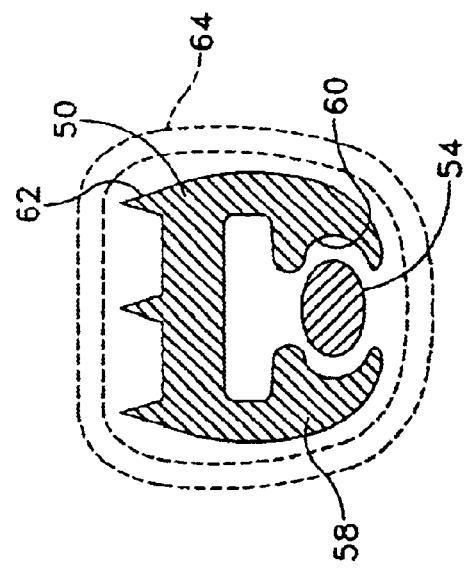

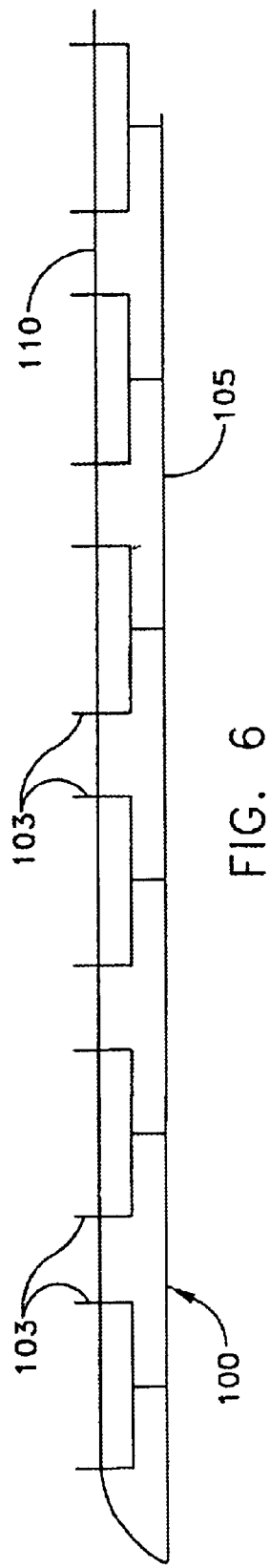
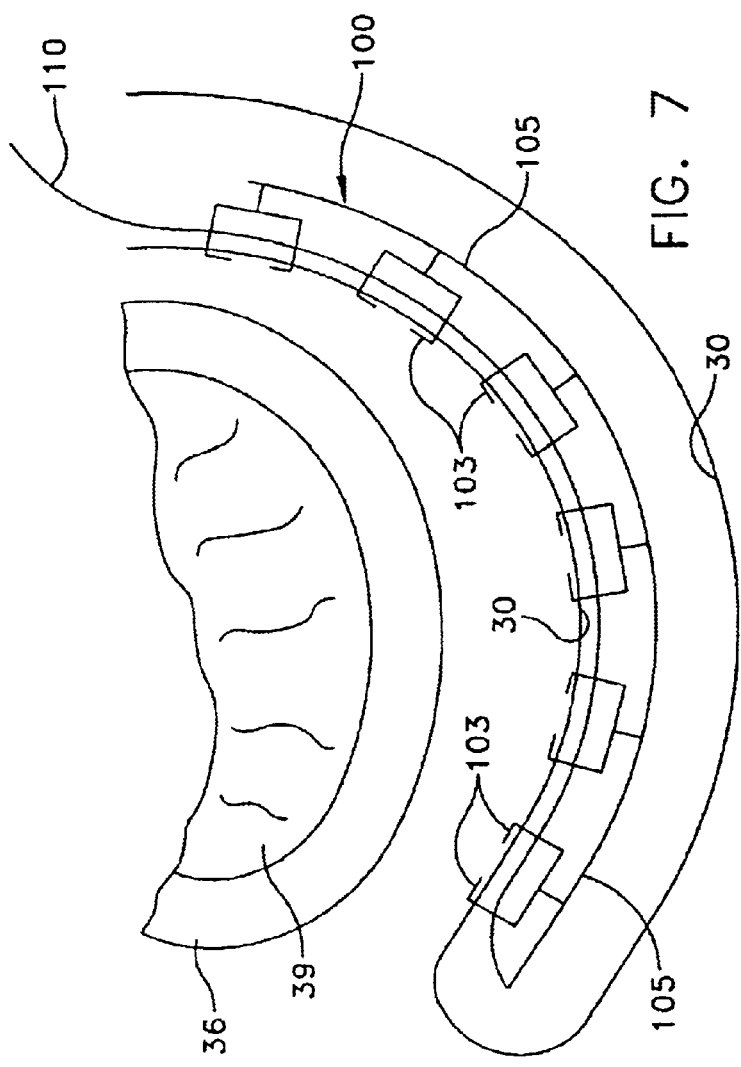

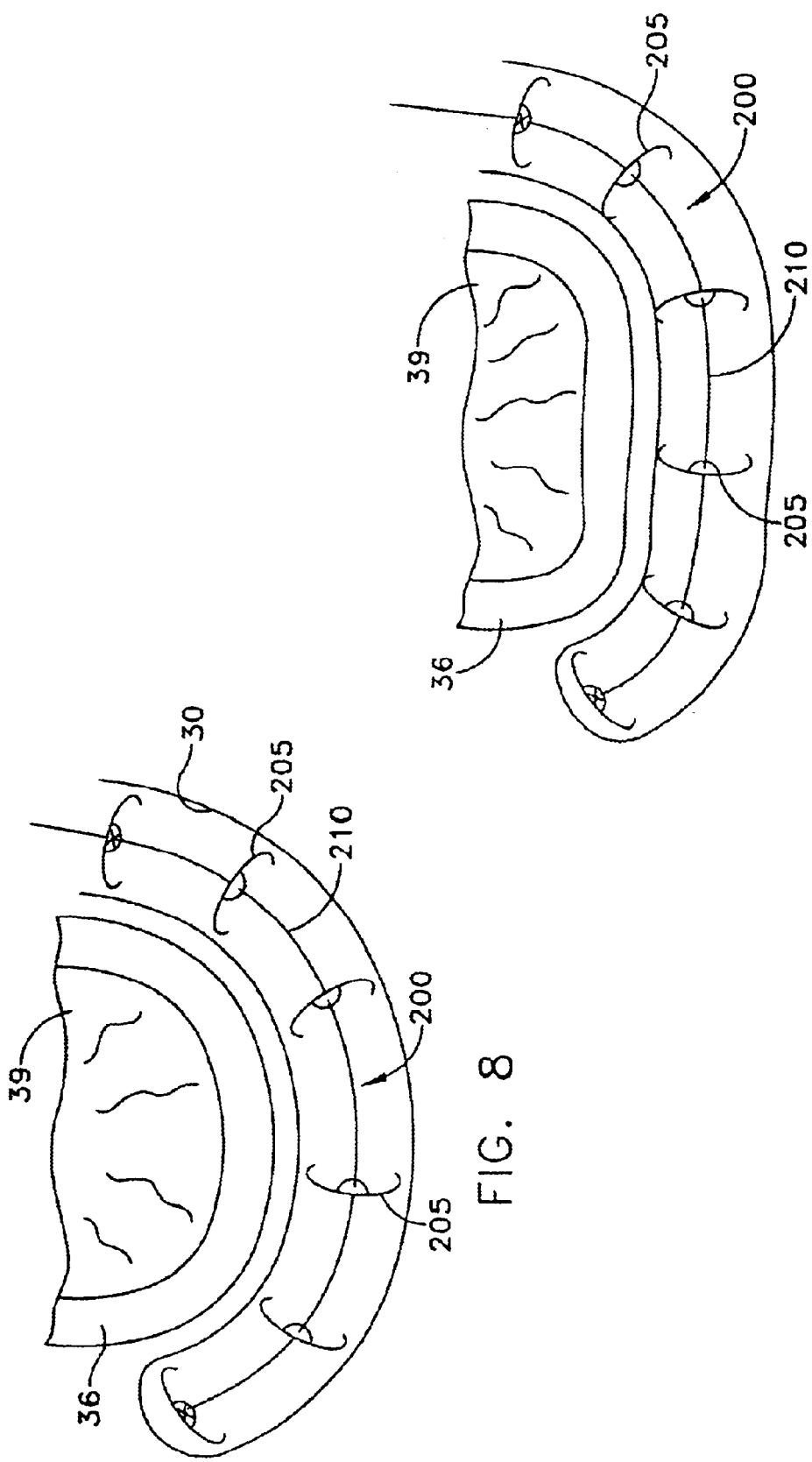

APPARATUS AND METHOD FOR REDUCING MITRAL REGURGITATION

REFERENCE TO RELATED APPLICATION

This patent application claims benefit of pending prior U.S. Provisional Patent Application Ser. No. 60/266,766, filed Feb. 5, 2001 by William E. Cohn et al. for TRANSVASCULAR APPROACH TO MITRAL VALVE PROCEDURES, which application is incorporated by reference herein.

BACKGROUND OF THE INVENTION

Mitral valve repair is the procedure of choice to correct mitral regurgitation of all etiologies. With the use of current surgical techniques, between 70% and 95% of regurgitant mitral valves can be repaired. The advantages of mitral valve repair over mitral valve replacement are well documented. These include better preservation of cardiac function and reduced risk of anticoagulant-related hemorrhage, thromboembolism and endocarditis.

In current practice, mitral valve surgery requires an extremely invasive approach that includes a chest wall incision, cardiopulmonary bypass, cardiac and pulmonary arrest, and an incision on the heart itself to gain access to the mitral valve. Such a procedure is associated with high morbidity and mortality. Due to the risk associated with this procedure, many of the sickest patients are denied the potential benefits of surgical correction of mitral regurgitation. In addition, patients with moderate, symptomatic mitral regurgitation are denied early intervention and undergo surgical correction only after the development of cardiac dysfunction.

Mitral regurgitation is a common occurrence in patients with heart failure and a source of important morbidity and mortality in these patients. Mitral regurgitation in patients with heart failure is caused by changes in the geometric configurations of the left ventricle, papillary muscles and mitral annulus. These geometric alterations result in mitral leaflet tethering and incomplete coaptation at systole. In this situation, mitral regurgitation is corrected by plicating the mitral valve annulus, either by (i) sutures alone or by (ii) sutures in combination with a support ring, so as to reduce the circumference of the distended annulus and restore the original geometry of the mitral valve annulus.

More particularly, current surgical practice for mitral valve repair generally requires that the posterior mitral valve annulus be reduced in radius by surgically opening the left atrium and then fixing sutures, or more commonly sutures in combination with a support ring, to the internal surface of the annulus; this structure is used to cinch the annulus, in a pursestring-like fashion, to a smaller radius, thereby reducing mitral regurgitation by improving leaflet coaptation.

This method of mitral valve repair, generally termed "annuloplasty", effectively reduces mitral regurgitation in heart failure patients. This, in turn, reduces symptoms of heart failure, improves quality of life and increases longevity. Unfortunately, however, the invasive nature of mitral valve surgery and the attendant risks render most heart failure patients poor surgical candidates. Thus, a less invasive means to increase leaflet coaptation and thereby reduce mitral regurgitation in heart failure patients would make this therapy available to a much greater percentage of patients.

Mitral regurgitation also occurs in approximately 20% of patients suffering acute myocardial infarction. In addition, mitral regurgitation is the primary cause of cardiogenic shock in approximately 10% of patients who develop severe hemodynamic instability in the setting of acute myocardial infarction. Patients with mitral regurgitation and cardiogenic shock have about a 50% hospital mortality. Elimination of mitral regurgitation in these patients would be of significant benefit. Unfortunately, however, patients with acute mitral regurgitation complicating acute myocardial infarction are particularly high-risk surgical candidates, and are therefore not good candidates for a traditional annuloplasty procedure. Thus, a minimally invasive means to effect a temporary reduction or elimination of mitral regurgitation in these critically ill patients would afford them the time to recover from the myocardial infarction or other acute life-threatening events and make them better candidates for medical, interventional or surgical therapy.

SUMMARY OF THE INVENTION

As a result, one object of the present invention is to provide an apparatus and method for treating mitral regurgitation which does not suffer from the disadvantages associated with conventional annuloplasty.

Another object of the present invention is to provide an apparatus and method for treating mitral regurgitation which can be deployed either permanently (e.g., for patients suffering from heart failure) or temporarily (e.g., for patients suffering from mitral regurgitation with acute myocardial infarction).

These and other objects are addressed by the present invention, which is made possible by the discovery that the mitral annulus may be remodeled without the plication of conventional, open-surgery annuloplasty.

With the above and other objects in view, a feature of the invention is the provision of an apparatus for reducing mitral regurgitation. The apparatus comprises a bendable elongated body adapted to be inserted into the coronary sinus of a patient in the vicinity of the posterior leaflet of the mitral valve, the elongated body being adjustable between a first configuration adapted to be delivered into the coronary sinus and a second configuration adapted to exert a force onto the posterior annulus. The body comprises a flexible spine having a proximal end and a distal end, and a flexible wire mounted on the spine and having a distal end fixed to the spine proximate to the distal end of the spine, and having a proximal portion extending from the proximal end of the spine. Axial movement of the wire causes a change in the spine from the first configuration to the second configuration to exert the force on the posterior annulus and thereby reduce mitral regurgitation.

In accordance with a further feature of the invention, there is provided a further apparatus for reducing mitral regurgitation. The apparatus comprises a bendable elongated body adapted to be inserted into the coronary sinus of a patient in the vicinity of the posterior leaflet of the mitral valve, the elongated body being adjustable between a first configuration adapted to be delivered into the coronary sinus and a second configuration adapted to exert a force onto the posterior annulus. The body comprises a flexible spine having a proximal end and a distal end, and a flexible wire mounted on the spine and having a distal end fixed to the spine proximate to the distal end of the spine, and having a proximal portion extending from the proximal end of the spine. Pulling of the wire causes straightening of the spine to move the spine from the first configuration to the second configuration to exert the force on the posterior annulus and thereby reduce mitral regurgitation.

In accordance with a further feature of the invention, there is provided a method for reducing mitral regurgitation. The method comprises the steps of positioning a prosthesis in a coronary sinus, the prosthesis comprising a bendable elongated body adapted to be inserted into the coronary sinus of a patient in the vicinity of the posterior leaflet of the mitral valve, the elongated body being adjustable between a first configuration adapted to be delivered into the coronary sinus and a second configuration adapted to exert a force onto the posterior annulus, the body comprising a flexible spine having a proximal end and a distal end, and a flexible wire mounted on the spine and having a distal end fixed to the spine proximate to the distal end of the spine, and having a proximal portion extending from the proximal end of the spine; and moving the wire axially to cause a change in the spine from the first configuration to the second configuration to exert the force on the posterior annulus and thereby reduce mitral regurgitation.

In accordance with a further feature of the invention, there is provided a further method for reducing mitral regurgitation, the method comprising the steps of positioning a prosthesis in a coronary sinus, the prosthesis comprising a bendable elongated body adapted to be inserted into the coronary sinus of a patient in the vicinity of the posterior leaflet of the mitral valve, the elongated body being adjustable between a first configuration adapted to be delivered into the coronary sinus and a second configuration adapted to exert a force onto the posterior annulus, the body comprising a flexible spine having a proximal end and a distal end, and a flexible wire mounted on the spine and having a distal end fixed to the spine proximate to the distal end of the spine, and having a proximal portion extending from the proximal end of the spine; and pulling the wire to straighten the spine and to move the spine from the first configuration to the second configuration to exert the force on the posterior annulus and thereby reduce mitral regurgitation.

In accordance with still further feature of the invention, there is provided a method for reducing mitral regurgitation, the method comprising scarring the mitral valve annulus to cause contraction thereof.

The above and other features of the invention, including various novel details of construction and combinations of parts and method steps, will now be more particularly described with reference to the accompanying drawings and pointed out in the claims. It will be understood that the particular devices and methods embodying the invention are shown by way of illustration only and not as limitations of the invention. The principles and features of this invention may be employed in various and numerous embodiments without departing from the scope of the invention.

BRIEF DESCRIPTION OF THE DRAWINGS

The above and other objects and features of the present invention are more fully disclosed by the following detailed description of the preferred embodiments of the invention, which is to be considered together with the accompanying drawings wherein like numbers refer to like parts and further wherein:

FIG. 3 is a side elevational, partly sectional view of a preferred apparatus formed in accordance with the present invention and shown in a first configuration;

FIG. 4 is a sectional view taken along line IV—IV of FIG. 3;

FIG. 6 is a diagrammatic illustration of an alternative embodiment in a first configuration;

FIG. 7 is a diagrammatic illustration of the embodiment of FIG. 6 in a second configuration;

FIG. 8 is a diagrammatic illustration of another alternative embodiment;

FIG. 9 is similar to FIG. 8, but illustrative of the embodiment of FIG. 8 in a second configuration.

DETAILED DESCRIPTION OF THE PREFERRED EMBODIMENTS

The coronary sinus is the largest vein in the human heart. During a large portion of its course in the atrioventricular groove, the coronary sinus typically extends adjacent to the left atrium of the heart for a distance of approximately 5 to 10 centimeters. Significantly, for a portion of its length, e.g., typically approximately 7–9 cm, the coronary sinus extends substantially adjacent to the posterior perimeter of the mitral annulus. The present invention takes advantage of this fact. More particularly, by deploying an elongated body in the coronary sinus, adjacent to the posterior leaflet of the mitral valve, pressure may be brought to bear on the posterior annulus of the mitral valve, whereby to move the posterior annulus anteriorly so as to improve leaflet coaptation and, as a result, reduce mitral regurgitation. In this respect it should be appreciated that the posterior annulus may be shifted anteriorly so as to achieve, or to attempt to achieve to the extent anatomically possible, leaflet-to-leaflet engagement or leaflet-to-annulus engagement (e.g., where a leaflet may be tethered due to left ventricular distortion). Both of these types of engagement, or targeted engagement, are intended to be encompassed by the terms "improved leaflet coaptation" and/or "increased leaflet coaptation" and the like.

In one preferred embodiment of the invention, access to the coronary sinus is gained percutaneously, e.g., the elongated body is introduced into the patient's vascular system via the jugular vein or via the left subclavian vein, passed down the superior vena cava, passed through the right atrium and then passed into the coronary sinus, where it is deployed. Alternatively, the elongated body may be introduced into the coronary sinus through a small incision in the heart, or through some other incision into the patient's vascular system.

Once deployed, the elongated body may be left in position permanently (e.g., in the case of patients suffering from mitral regurgitation associated with heart failure) or the elongated body may be left in position only temporarily (e.g., in the case of patients suffering from mitral regurgitation associated with acute myocardial infarction).

Visualization of the procedure may be obtained by fluoroscopy, echocardiography, intravascular ultrasound, angioscopy, real-time magnetic resonance imaging, etc. The efficacy of the procedure may be determined through echocardiography, although other imaging modalities may also be suitable.

Figure 1:
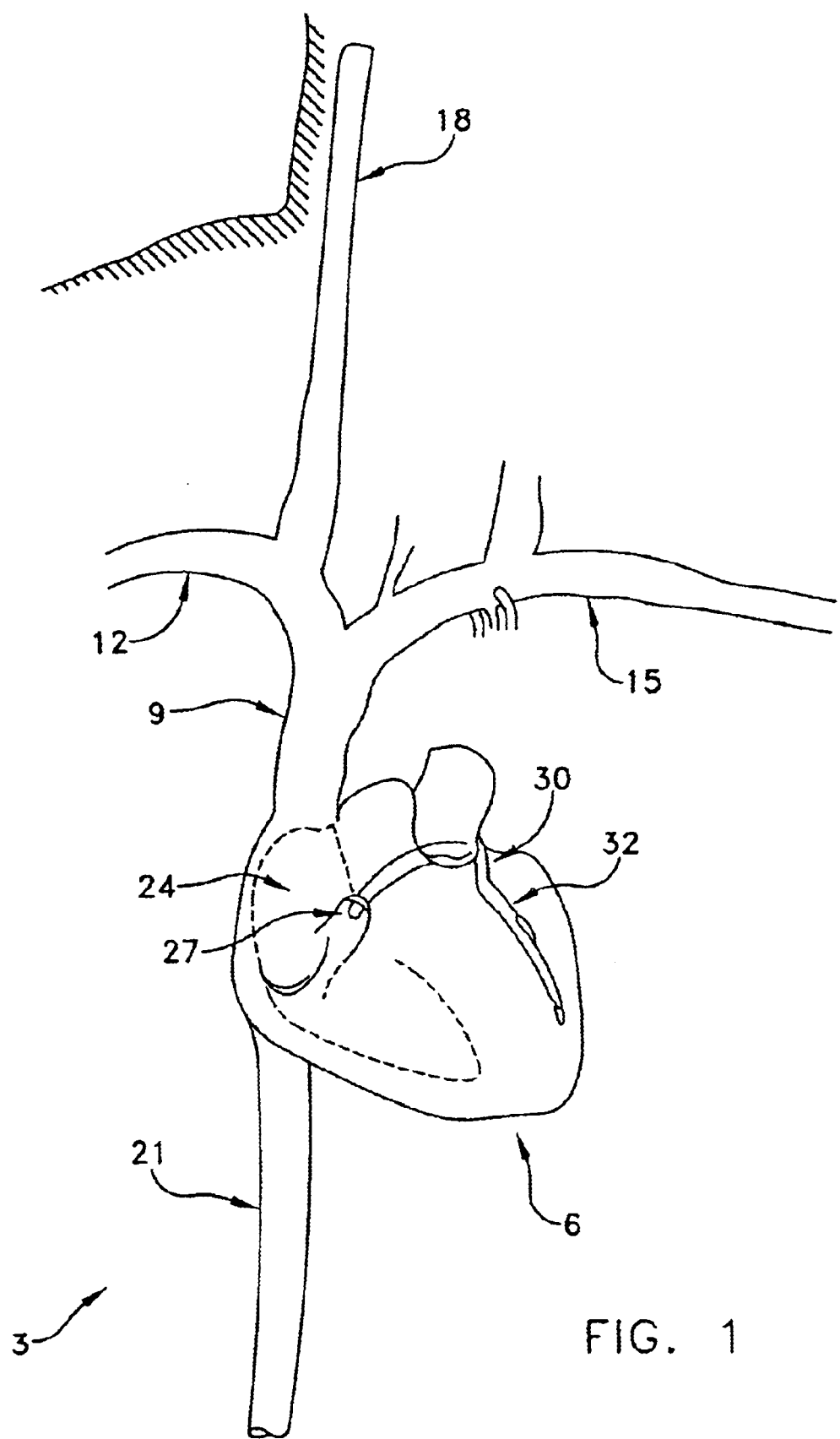
FIG. 1 is a schematic view of portions of the human vascular system.

Looking now at FIG. 1, there are shown aspects of the cardiovascular system 3 of a patient. More particularly, cardiovascular system 3 generally comprises the heart 6, the superior vena cava 9, the right subclavian vein 12, the left subclavian vein 15, the jugular vein 18, and the inferior vena cava 21. Superior vena cava 9 and inferior vena cava 21 communicate with the heart's right atrium 24. The coronary ostium 27 leads to coronary sinus 30. At the far end 31 (FIG. 2) of coronary sinus 30, the vascular structure turns into the vertically-descending anterior interventricular vein ("AIV") 32 (see FIG. 1). For purposes of the present invention, it can generally be convenient to consider the term "coronary sinus" to mean the vascular structure extending between coronary ostium 27 and AIV 32.

Figure 2:
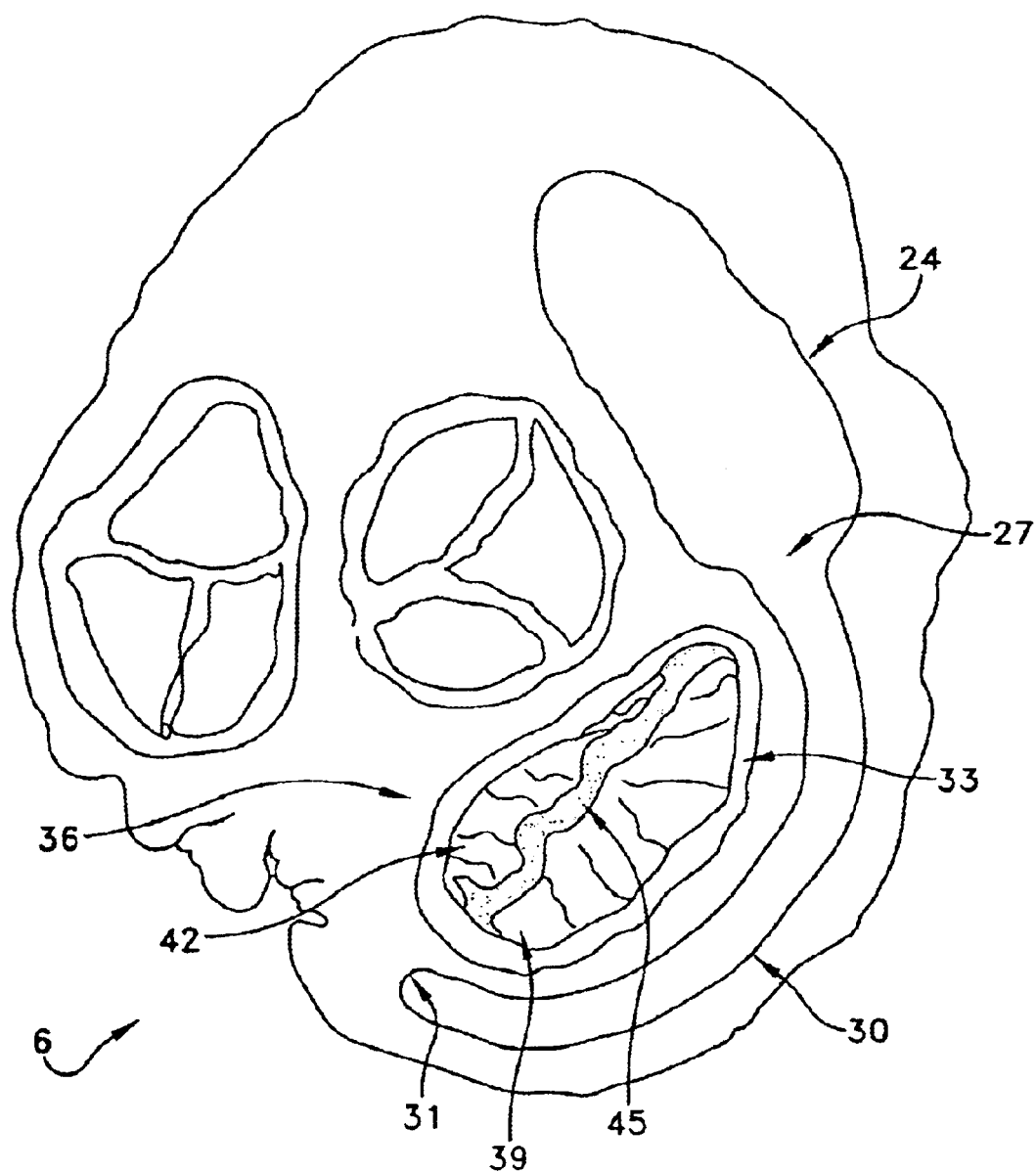
FIG. 2 is a schematic view of portions of the human heart.

As seen in FIG. 2, between coronary ostium 27 and AIV 32, coronary sinus 30 generally extends substantially adjacent to the posterior perimeter of the annulus 33 of the mitral valve 36. Mitral valve 36 comprises a posterior leaflet 39 and an anterior leaflet 42. In the case of a regurgitant mitral valve, posterior leaflet 39 and anterior leaflet 42 will generally fail to properly coapt at systole, thereby leaving an intervening gap 45 which will permit regurgitation.

Figure 5:
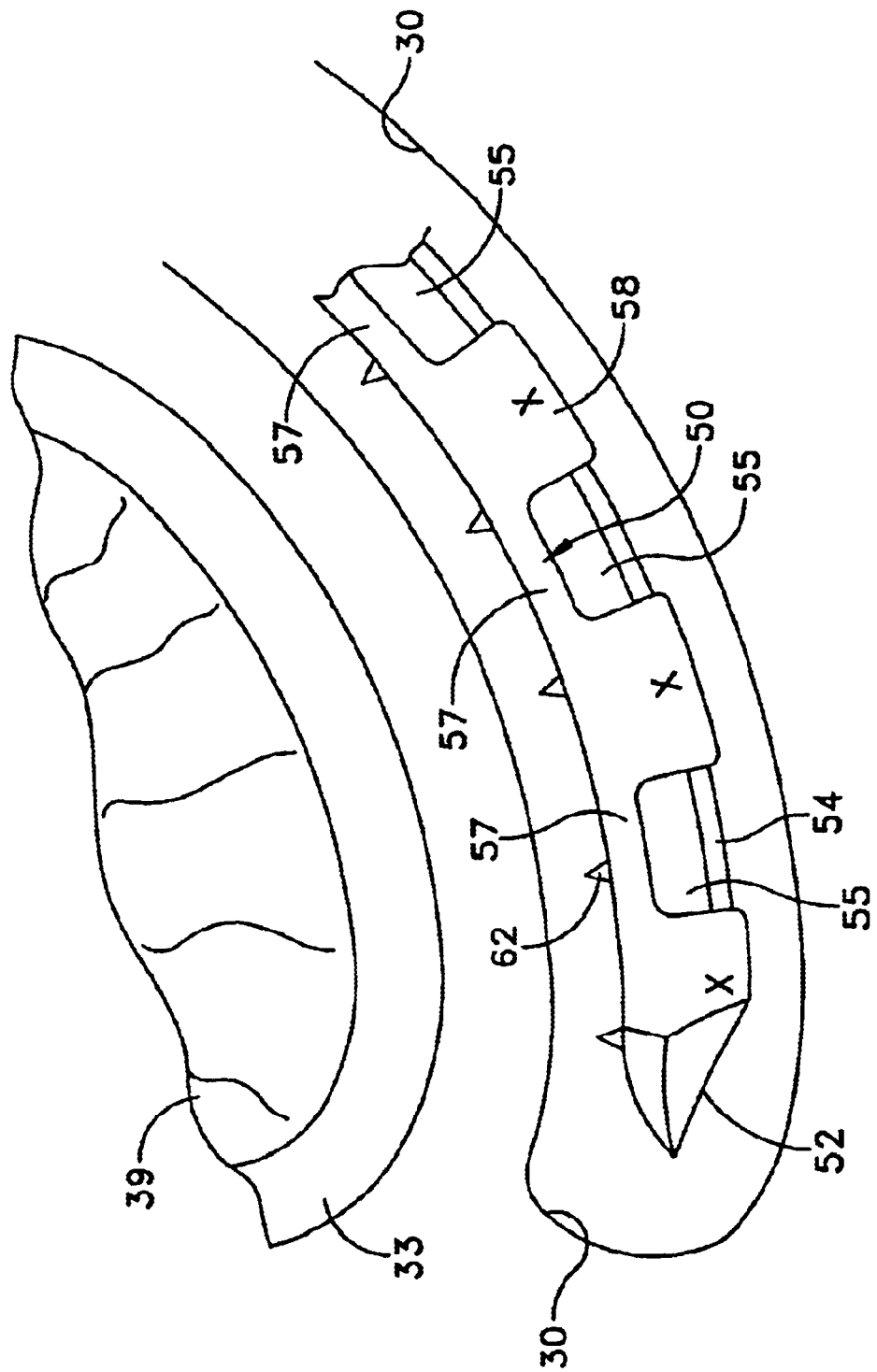
FIG. 5 is a side elevational view of the apparatus of FIG. 3 shown in a second configuration.

Referring to FIG. 3, it will be seen that an illustrative preferred embodiment includes an elongated flexible body 50. The body 50 preferably is provided with a rounded or pointed distal end 52 for insertion into the coronary sinus 30 (FIG. 5).

Fixed to the distal end 52 of the body 50 is a wire 54 which extends through the body 50, with a proximal portion 56 thereof extending proximally from body 50 (FIG. 3). The body 50 is provided with wire supporting portions 58, each of which defines a channel 60 (FIG. 4) for retaining the wire 54, but permitting the wire 54 to slide therethrough. Wire 54 is preferably positioned on one side of the longitudinal axis of body 50, and body 50 preferably includes a plurality of openings 55 helping to define a plurality of flexible bridges 57.

The body 50 may be provided with barbs 62 for engagement with tissue in the coronary sinus 30. When barbs 62 are used, the elongated body 50 should be housed in a guide catheter 64 (FIG. 4) which is removed once the body 50 is in place, to expose barbs 62.

As body 50 is inserted into coronary sinus 30, it will generally assume the shape of the coronary sinus, which is naturally curved in the region of the posterior leaflet of the mitral valve. Thereafter, wire 54 may be pushed or pulled, as desired, so as to alter the configuration of body 50. More specifically, by pushing the wire 54 in a distal direction, the body 50 is caused to reconfigure to a tighter arc around the mitral valve annulus 33, i.e., by bending on bridges 57 and enlarging openings 55. By pulling the wire 54 proximally, the body is caused to reconfigure to a more extended arc, or to assume a straight configuration, or even to assume an inverted configuration, by bending on bridges 57 and reducing openings 55. Either alteration of the configuration of body 50 in turn alters the configuration of the coronary sinus adjacent to the mitral valve, whereby to force the posterior annulus anteriorly and thereby improve leaflet coaptation and hence reduce mitral regurgitation.

Looking next at FIG. 6, there is shown an alternative embodiment of the present invention. More particularly, there is shown an elongated body 100 which comprises a plurality of staples 103 connected by a flexible bridge 105. A wire 110 has one end secured to the distalmost end of bridge 105. During use, the elongated body 100 is positioned within the coronary sinus (FIG. 7), staples 103 are secured to the walls of the coronary sinus 30, and then wire 110 is pushed distally or pulled proximally so as to modify the configuration of elongated body 100. More particularly, pulling wire 110 proximally will cause bridge 105 to reconfigure to a tighter arc around the mitral valve annulus, whereas pushing wire 110 distally will cause bridge 105 to reconfigure into a more extended arc, or to go straight, or even to invert. This action in turn alters the configuration of the coronary sinus 30 adjacent to the mitral valve 36, whereby to force the posterior annulus anteriorly and thereby improve leaflet coaptation and hence reduce mitral regurgitation.

Looking next at FIG. 8, there is shown another alternative embodiment of the present invention. More particularly, there is shown an elongated body 200 which comprises a plurality of anchors 205, formed by staples, or the like, each comprising an eyelet through which extends a wire 210. The distal end of wire 210 is secured to the distalmost staple. During use, the elongated body 200 is positioned within the coronary sinus, the anchors 205 are secured to the walls of the coronary sinus 30, and then wire 210 is pulled proximally so as to modify the configuration of elongated body 200. More specifically, pulling of the wire 210 causes the body 200 to reconfigure to a wider arc (FIG. 9) and then, if pulled further, to a substantially straight configuration. Such action, in turn, alters the configuration of the coronary sinus 30 adjacent to the mitral valve 36, whereby to force the posterior annulus anteriorly and thereby improve leaflet coaptation and hence reduce mitral regurgitation.

Figure 10:
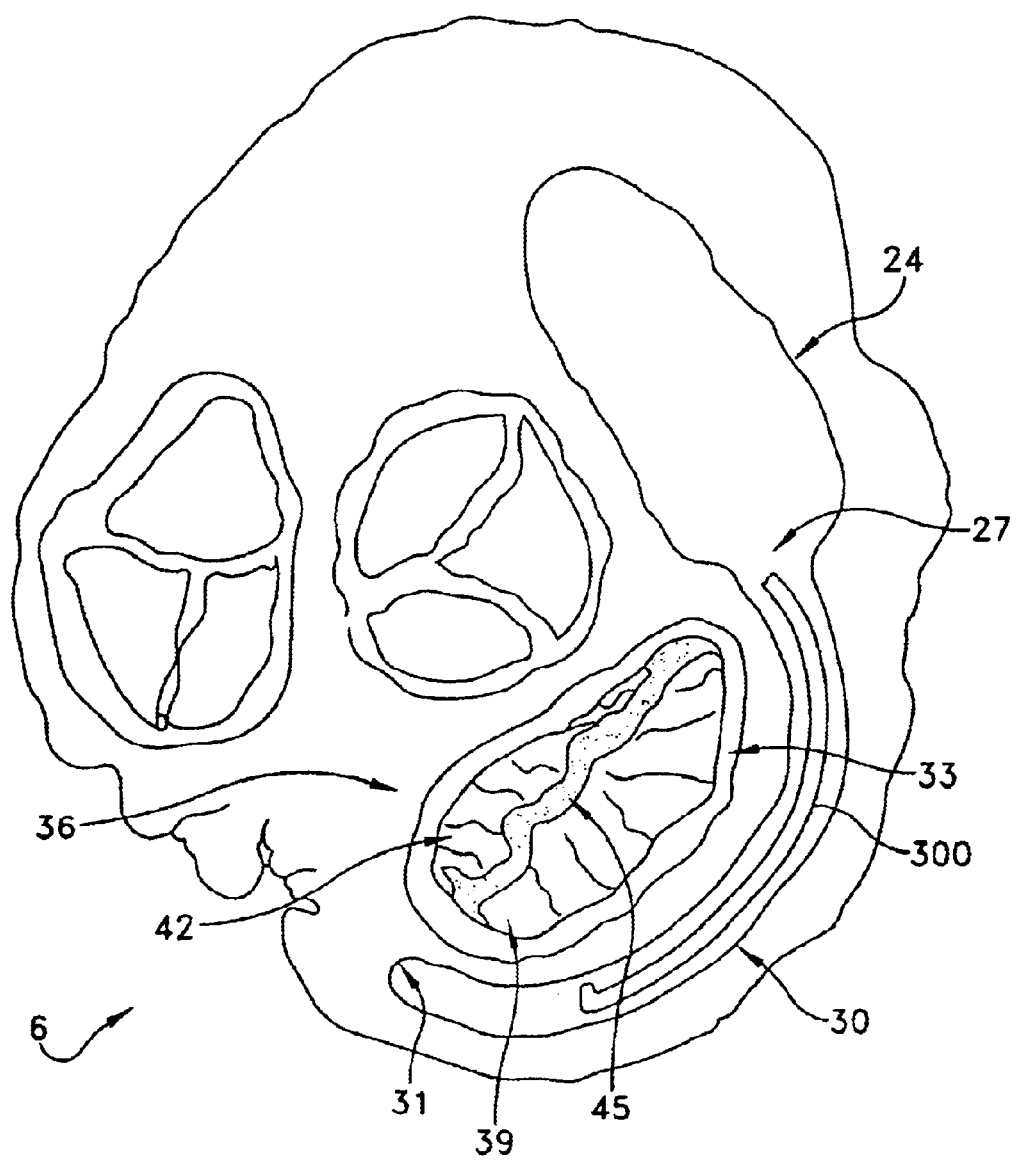
FIG. 10 is a schematic view of portions of the human heart and illustrating diagrammatically another alternative embodiment of the invention.

Looking next at FIG. 10, there is shown another embodiment of the present invention. More particularly, there is shown an elongated body 300 which is adapted to reducing mitral regurgitation by scarring the mitral valve annulus 33 to cause contraction thereof. Elongated body 300 includes an element at its distal end which is adapted to inject a scarring medium into the mitral valve annulus. This scarring medium may comprise a chemical, or it may comprise energy selected from a group of energies consisting of thermal, cryogenic, laser and radio frequency.

It is to be understood that the present invention is by no means limited, to the particular constructions and method steps herein disclosed and/or shown in the drawings, but also comprises any modifications or equivalents within the scope of the claims.

What is claimed is:

1. Apparatus for reducing mitral regurgitation, the apparatus comprising:

a bendable elongated body adapted to be inserted into the coronary sinus of a patient in the vicinity of the posterior leaflet of the mitral valve, the elongated body being adjustable between a first configuration adapted to be delivered into the coronary sinus and a second configuration adapted to exert a force onto the posterior annulus, the body comprising:

a flexible spine having a proximal end and a distal end, said flexible spine forming a longitudinal axis from said proximal end to said distal end, a plurality of wire supporting portions extending transversely from said spine, each said portion defining a channel therethrough, said plurality of wire supporting portions defining a plurality of openings therebetween, and a plurality of flexible bridges connecting said plurality of wire supporting portions to one another; and a flexible wire slideably mounted through said plurality of wire supporting portions extending from said spine and having a distal end fixed to said spine proximate to the distal end of said spine, and having a proximal portion extending from the proximal end of said spine;

whereby axial movement of said wire causes a change in said spine from the first configuration to the second configuration to exert the force on the posterior annulus and thereby reduce mitral regurgitation.

2. The apparatus in accordance with claim 1, wherein the axial movement of said wire through said plurality of wire supporting portions in a proximal direction causes said spine reconfiguration to a lesser curve having a greater radius of curvature.

3. The apparatus in accordance with claim 1 wherein the axial movement of said wire in a distal direction through said plurality of wire supporting portions causes said spine to reconfigure to a more pronounced curve having a lesser radius of curvature.

4. The apparatus in accordance with claim 1 wherein the first configuration is curved and the second configuration is a selected one of (i) more curved and (ii) less curved.

5. The apparatus in accordance with claim 4 wherein the selected one of the second configuration is the less curved configuration, and further wherein the less curved configuration is substantially straight.

6. The apparatus in accordance with claim 1 wherein said spine is provided with barbs thereon.

7. Apparatus for reducing mitral regurgitation, the apparatus comprising:
   a bendable elongated body adapted to be inserted into the coronary sinus of a patient in the vicinity of the posterior leaflet of the mitral valve, the elongated body being adjustable between a first configuration adapted to be delivered into the coronary sinus and a second configuration adapted to exert a force onto the posterior annulus, the body comprising:
      a flexible spine having a proximal end and a distal end; and
      a flexible wire mounted on said spine and having a distal end fixed to said spine proximate to the distal end of said spine, and having a proximal portion extending from the proximal end of said spine;
      whereby pulling of said wire causes straightening of said spine to move said spine from the first configuration to the second configuration to exert the force on the posterior annulus and thereby reduce mitral regurgitation.

8. The apparatus in accordance with claim 7, wherein loops are mounted on said spine and said wire is movable therein.

9. The apparatus in accordance with claim 8, wherein said loops are staples.

10. Apparatus for reducing mitral regurgitation, the apparatus comprising:
   a bendable elongated body adapted to be inserted into the coronary sinus of a patient in the vicinity of the posterior leaflet of the mitral valve, the elongated body being adjustable between a first configuration adapted to be delivered into the coronary sinus and a second configuration adapted to exert a force onto the posterior annulus, the body comprising:
      a flexible spine having a proximal end and a distal end; and
      a flexible wire mounted on said spine and having a distal end fixed to said spine proximate to the distal end of said spine, and having a proximal portion extending from the proximal end of said spine;
      whereby axial movement of said wire causes a change in said spine from the first configuration to the second configuration to exert the force on the posterior annulus and thereby reduce mitral regurgitation;
      wherein the axial movement of said wire in a proximal direction causes said spine reconfiguration to a lesser curve having a greater radius of curvature.

11. Apparatus for reducing mitral regurgitation, the apparatus comprising:
   a bendable elongated body adapted to be inserted into the coronary sinus of a patient in the vicinity of the posterior leaflet of the mitral valve, the elongated body being adjustable between a first configuration adapted to be delivered into the coronary sinus and a second configuration adapted to exert a force onto the posterior annulus, the body comprising:
      a flexible spine having a proximal end and a distal end; and
      a flexible wire mounted on said spine and having a distal end fixed to said spine proximate to the distal end of said spine, and having a proximal portion extending from the proximal end of said spine;
      whereby axial movement of said wire causes a change in said spine from the first configuration to the second configuration to exert the force on the posterior annulus and thereby reduce mitral regurgitation;
      wherein the axial movement of said wire in a distal direction causes said spine to reconfigure to a more pronounced curve having a lesser radius of curvature.

12. Apparatus for reducing mitral regurgitation, the apparatus comprising:
   a bendable elongated body adapted to be inserted into the coronary sinus of a patient in the vicinity of the posterior leaflet of the mitral valve, the elongated body being adjustable between a first configuration adapted to be delivered into the coronary sinus and a second configuration adapted to exert a force onto the posterior annulus, the body comprising:
      a flexible spine having a proximal end and a distal end; and
      a flexible wire mounted on said spine and having a distal end fixed to said spine proximate to the distal end of said spine, and having a proximal portion extending from the proximal end of said spine;
      whereby axial movement of said wire causes a change in said spine from the first configuration to the second configuration to exert the force on the posterior annulus and thereby reduce mitral regurgitation;
      wherein loops are fixed to said spine and said wire extends through said loops and is movable therethrough.

13. Apparatus for reducing mitral regurgitation, the apparatus comprising:
   a bendable elongated body adapted to be inserted into the coronary sinus of a patient in the vicinity of the posterior leaflet of the mitral valve, the elongated body being adjustable between a first configuration adapted to be delivered into the coronary sinus and a second configuration adapted to exert a force onto the posterior annulus, the body comprising:
      a flexible spine having a proximal end and a distal end; and
      a flexible wire mounted on said spine and having a distal end fixed to said spine proximate to the distal end of said spine, and having a proximal portion extending from the proximal end of said spine;
      whereby axial movement of said wire causes a change in said spine from the first configuration to the second configuration to exert the force on the posterior annulus and thereby reduce mitral regurgitation;
      wherein loops are fixed to said spine and said wire extends through said loops and is movable therethrough; and
      wherein the loops are defined by staples.

* * * * *